United States Patent [19]

Kavasmaneck et al.

[11] 4,297,241
[45] Oct. 27, 1981

[54] METHOD OF PREPARING AN OLEFIN HYDRATION CATALYST

[75] Inventors: Percy R. Kavasmaneck; David B. Stanton; Paul D. Sherman, Jr., all of South Charleston, W. Va.

[73] Assignee: Union Carbide Corporation, New York, N.Y.

[21] Appl. No.: 132,496

[22] Filed: Mar. 21, 1980

[51] Int. Cl.³ .................. B01J 21/08; B01J 21/12; B01J 27/16
[52] U.S. Cl. ................................ 252/435; 568/896
[58] Field of Search .................... 252/435; 568/896

[56] References Cited

U.S. PATENT DOCUMENTS

| | | | |
|---|---|---|---|
| 2,840,530 | 6/1958 | Milliken et al. | 252/455 R |
| 2,960,477 | 11/1960 | Smith et al. | 252/435 |
| 3,311,568 | 3/1967 | Klimenko | 252/435 |
| 3,459,678 | 8/1969 | Hagemeyer et al. | 252/435 |
| 3,862,249 | 1/1975 | Ester et al. | 252/435 |

*Primary Examiner*—W. J. Shine
*Attorney, Agent, or Firm*—Bernard F. Crowe

[57] ABSTRACT

Olefins can be hydrated to the corresponding alcohols with a hydration catalyst comprising a calcined support consisting of diatomaceous earth, bentonite, silica, cornmeal and cellulose which has been calcined and then impregnated with phosphoric acid.

2 Claims, No Drawings

METHOD OF PREPARING AN OLEFIN HYDRATION CATALYST

BACKGROUND OF THE INVENTION

This invention pertains to an improved process for hydrating olefins and more particularly to a phosphoric acid supported catalyst which has both high activity and high crush strength.

Supported phosphoric acid catalysts have been widely and successfully employed commercially for the past 30 years in the direct hydration of ethylene to ethanol, as well as the direct hydration of other olefins. Different silica based supports have been used including diatomaceous earth, usually in conjunction with a clay binder, silica gel and various alumino silicates. Generally the support is calcined to impart physical integrity and then leached with a mineral acid to reduce the content of metallic impurities prior to impregnation with phosphoric acid.

Although phosphoric acid catalysts, such as those described above, have been used commercially, there is a continuing need for an olefin hydration catalyst which combines several properties, viz., reasonably long life regarding its catalytic activity, sufficient mechanical strength to withstand crushing during preparation and use, and chemical stability and inertness during the hydration process.

SUMMARY OF THE INVENTION

An olefin hydration catalyst having enhanced catalytic activity without loss of cumulative crush strength has been found by (1) mixing a composition comprising 30 to 70 parts by weight of diatomaceous earth, 15 to 30 parts by weight of bentonite, 15 to 30 parts by weight of synthetic high surface area silica, 5 to 25 parts by weight of cornmeal and 5 to 25 parts by weight of cellulose with sufficient water to form a paste;

(2) extruding the above composition from a pellet mill;

(3) drying the pellets at about 250° C. for 1 hour;

(4) calcining the pellets for 30 minutes at about 677° C.;

(5) leaching the pellets of step (4) free of metallic impurities with 85% phosphoric acid under reflux for eight hours;

(6) washing the pellets from step (5) with water until neutral;

(7) drying the pellets;

(8) impregnating the pellets from step (7) with 65% aqueous phosphoric acid at room temperature;

(9) draining off excess phosphoric acid; and

(10) drying the pellets at a temperature of about 100° to about 400° C.

The diatomaceous earth used in the instant catalyst composition is a naturally occuring form of silicon dioxide. A preferred form of diatomaceous earth is "Celite FC" manufactured by Johns-Manville Corporation and having a surface area of 20–30 m²/g. This material has the following average composition

| Component | Weight Percent |
| --- | --- |
| $SiO_2$ | 86.7 |
| $Al_2O_3$ | 3.3 |
| $Fe_2O_3$ | 1.2 |
| CaO | 0.5 |

-continued

| Component | Weight Percent |
| --- | --- |
| $H_2O$, trace metal oxides | 8.3 |

Bentonite preferably having a particle size distribution such that about 90% of the particles are below 74 microns, is a hydrated alumino silicate having the following average composition:

| Component | Weight Percent |
| --- | --- |
| $SiO_2$ | 49.0 |
| $Al_2O_3$ | 20.4 |
| $Fe_2O_3$ | 4.1 |
| CaO | 1.8 |
| $H_2O$, trace metal oxides | 24.7 |

The silica used is hydrophilic, precipitated silica having a surface area of about 150 meters²/gram.

The cornmeal used is polenta grade.

Cellulose is obtained from the chemical treatment of cotton in a form of white fibers which treatment removes the other plant constituents from the cotton. It is a polysaccharide having the empirical formula $C_6H_{10}O_5$.

By using a relatively low support calcination temperature, that is, from about 650° to about 730° C. an improved support silanol-acid interaction is obtained affording a more active hydration catalyst, without sacrificing the crush strength. The lower calcination temperature also permits more efficient removal of metallic impurities from the support resulting in much lower metals content, i.e., less than about 0.3 weight percent in the catalyst. These calcination conditions permit a full oxidation of the cornmeal and cellulose without resulting in sintering of the support.

The leaching of the calcined support prior to impregnation with phosphoric acid removes metallic impurities particularly aluminum oxide, iron oxide, and calcium oxide, which are soluble in phosphoric acid under normal operating conditions and can cause clogging of the pores with phosphate salts ultimately resulting in loss of catalyst activity. While many strong mineral acids have been recommended for this leaching process, including hydrochloric acid, phosphoric acid, and the like, it has been found that 85% phosphoric acid affords the lowest level of metallic impurities in the catalyst support which is necessary for commercial hydration of olefins under actual plant conditions.

Impregnation of the calcined support is carried out in an aqueous solution of phosphoric acid containing from about 40 to about 80 percent by weight of phosphoric acid. The impregnation can be effected in any manner which will result in substantial saturation of the support material with phosphoric acid catalyst. One preferred method is to soak the support material in the aqueous phosphoric acid at a temperature of about 30° C. for a period of time from about 0.5 hours to about 8 hours. Generally, a period of about 2 hours is sufficient. After removing excess phosphoric acid and drying at a temperature of about 100° to about 400° C., the phosphoric acid impregnated support contains from about 30 to about 60 percent by weight of orthophosphoric acid based on the weight of the composite structure, i.e., support material plus acid catalyst.

Lower olefins, such as, ethylene, propylene and the butenes, may be directly hydrated to the corresponding alcohols, i.e., ethanol, or isopropanol and 2-butanol by reacting the olefin with water vapor in the presence of the above-described catalyst at a temperature within the range of about 220° to about 300° C., a water vapor to olefin mole ratio of about 0.3 to about 3.0, and an operating pressure of about 500 to about 1200 psig. Preferred operating conditions for the conversion of ethylene to ethanol consists of a temperature of about 250°-290° C., a water vapor to olefin mole ratio of about 1 to about 0.3, and a reaction pressure of about 900 to about 1100 psig. Lower temperatures and higher pressures favor high equilibrium yields. However, if temperatures are too low, reaction rates decrease, while unduly high pressures result in relatively large amounts of polymeric material in the reaction product mixture. Higher water vapor to olefin mole ratios result in improved conversion, but at the expense of increased energy requirements for vaporization.

While not intending to be bound by any theoretical explanation of the superior catalyst properties obtained by this invention, it is believed that the use of one organic compound (cellulose) and one inorganic compound (silica) in preparing the catalyst affords a fortuitous increase in surface and decrease in mean pore radius over previously available olefin hydration catalysts. Thus when a preferred composition is made using 50 parts by weight of Celite FC, 25 parts by weight of bentonite, 25 parts by weight of Hi Sil, 10 parts by weight of cornmeal and 10 parts by weight of cellulose a catalyst having the following properties is obtained:

| | |
|---|---|
| PELLET SIZE | 1/8" × 1/4" |
| CALCINATION TEMP., °C. | 677 |
| SUPPORT SURFACE AREA, M$^2$/GM | 60 |
| SUPPORT POROSITY, CC/GM | 0.67 |
| SUPPORT MEAN PORE RADIUS, $\mu$ | 0.015 |
| ACID LOADING, WT. PERCENT | 48 |
| METALS CONTENT, WT. PERCENT | 0.2 |
| CATALYST CRUSH STRENGTH, LBS. | 18 |

Supports containing only silica have higher surface areas (>200 meters$^2$/gram) but are very weak. It was surprising to find that the use of hydrophilic silica in a diatomaceous earth-based support affords an active olefin hydration catalyst without a loss in crush strength.

It is believed that the critical combination of low calcination temperatures, low metals level achieved by phosphoric acid leaching, high crush strength and high surface area provide a unique and active olefin hydration catalyst.

The invention is further described in the examples which follow. All parts and percentages are by weight unless otherwise specified.

EXAMPLE 1

Fifty (50) parts by weight of diatomaceous earth (identified as Celite FC a trademark of Johns Manville Corp.), 25 parts by weight of bentonite, 25 parts by weight of Hi Sil 233 (a trademark of PPG Industries for a hydrophilic precipitated silica having a surface area of 150 m$^2$/g.), 10 parts by weight of cornmeal (Polenta grade) and 10 parts by weight of cellulose, were admixed with water to form pellets which were 1/8" in diameter. The pellets were dried at 350° F. for 30 minutes to remove moisture and then calcined in air for 40 minutes at 1300° F. The surface area of the support (as measured by BET nitrogen) was 60 m$^2$/gm, mean pore radius was 0.015$\mu$, and metallic impurity level (of Fe and Al oxides) was 4.5 weight percent. Following calcination, the support was treated with 80 percent H$_3$PO$_4$ under reflux conditions for 8 hours to reduce metallic impurities to 0.5 weight percent. The leached support was then washed with water at 90° C. for 2 hours. The leached support was then dried with an inert gas at 140° C. for 18 hours and then impregnated with 65 percent H$_3$PO$_4$ at room temperature for 8 hours. The excess acid was allowed to drain off and the catalyst pellets were dried under inert conditions at 110° C. for 18 hours.

EXAMPLE 2

Example 1 was repeated, except that the leaching step was undertaken with 80 percent H$_3$PO$_4$, but at 185° F. for 120 hours.

EXAMPLE 3

A gaseous mixture of ethylene and steam in the molar ratio of 1.9:1 was passed over the catalyst of Example 1 and 2 at the rate of 2000 SCFH/ft$^3$ of catalyst. The pressure in the backmixed, stirred autoclave was 1000 psig and the temperature of the catalyst bed was maintained at 270° C. At the end of 28 hours, peak activity was attained and an ethanol production rate of 9.4 lbs/hr/cu. ft was obtained in each case.

CONTROL A

A catalyst having the composition disclosed in Example 1, but leached with a 1:1 HCl at 85° C. for 120 hours reduces metallic impurity levels to only 1.2 wt percent. Peak productivity of this catalyst under the reaction conditions described in Example 3 is only 8.6 lbs/hr/cu ft.

CONTROL B

A catalyst having the following composition: 62 parts by weight of diatomaceous earth, 21 parts by weight of bentonite and 17 parts by weight of cornmeal (viz., the composition disclosed in Example 1 minus Hi Sil and Cellulose) was admixed with water to form pellets which were 5/32" in diameter. The pellets were dried as in Example 1 but were calcined for 40 minutes at a slightly higher temperature, i.e., 732° C. The surface area of this support was 13 m$^2$/gm, mean pore radius was 0.3$\mu$ and metallic impurity level was 4.75 weight percent. After leaching and washing as prescribed in Examples 1, 2 or 4 (viz., with H$_3$PO$_4$ or HCl), the metallic content was reduced to 2 weight percent. Drying, impregnation with H$_3$PO$_4$ and final roasting was undertaken as described in Example 1. The catalyst of this example when tested under conditions of Example 3, had a peak activity of only 8.3 lbs of ethanol/hr/cu. ft of catalyst.

EXAMPLE 4

When catalyst of Example 1 was operated in a tubular reactor under conditions described in Example 3, but an inlet temperature of 255° C. and outlet of 275° C., peak ethanol production rate of 10 lbs/hr/cu. ft were attained after 200 hours of operation and production remained essentially unchanged after 700 hours.

When catalyst of CONTROL B was operated under these conditions a peak production rate of only 8.5 lbs/hr/cu. ft was attained after 200 hours and this production rate remained unchanged after 700 operating hours.

EXAMPLE 5

When catalyst of Example 1 was operated under conditions of Example 3, except at lower space velocity, of 1600 SCFH/cu. ft$^3$ catalyst, peak ethanol productivity was 8.2 lbs/hr/cu. ft.

With the catalyst of CONTROL B, peak productivity was 7.2 lbs/hr/cu. ft.

EXAMPLE 6

When catalyst of Example 1 was operated under conditions outlined in Example 3 but at a lower temperature of 260° C., peak ethanol productivity was 8.3 lbs/hr/cu. ft.

With catalyst of CONTROL B peak productivity was 7.0 lbs/hr/cu. ft.

EXAMPLE 7

To illustrate the crush strength superiority over state of the art, steamed silica gel catalysts of (U.S. Pat. No. 4,038,211)

| Catalyst form (dry) | Crush Strength (in lbs.) | | |
|---|---|---|---|
| | Example 1 | Silica Gel (Prior Art) unsteamed | steamed |
| Support | 15 | 9 | 9 |
| Catalyst | 18 | 2.7 | 6.1 |

Although the invention has been described in its preferred form with a certain degree of particularity, it is understood that the present disclosure has been made only by way of example and that numerous changes can be made without departing from the spirit and the scope of the invention.

What is claimed is:

1. Method of preparing an olefin hydration catalyst which comprises the steps of:
    (1) blending a mixture of about 30 to about 70 parts by weight of diatomaceous earth, about 15 to about 30 parts by weight of bentonite, about 15 to about 30 parts by weight of a synthetic silica having a surface area of about 150 to about 200 meters$^2$ per gram, about 5 to about 25 parts by weight of cornmeal and about 5 to about 25 parts by weight of cellulose with sufficient water to form a paste;
    (2) extruding the paste from step 1 into pellets;
    (3) drying said pellets;
    (4) calcining said dried pellets at a temperature of about 650° to about 730° C.;
    (5) leaching the calcined pellets with aqueous 85 percent phosphoric acid until metallic impurities are reduced to a minimum;
    (6) washing the leached pellets with water until the wash water is approximately neutral;
    (7) drying the pellets;
    (8) impregnating the dried pellets with 65 percent phosphoric acid at room temperature;
    (9) draining off excess phosphoric acid; and
    (10) drying the pellets at a temperature of about 100° to about 400° C.

2. Method claimed in claim 1 wherein the paste is made from about 50 parts by weight of diatomaceous earth, about 25 parts by weight of bentonite, about 25 parts by weight of synthetic silica, about 10 parts by weight of cornmeal and about 10 parts by weight of cellulose.

* * * * *